United States Patent [19]
Animati et al.

[11] Patent Number: 5,472,976
[45] Date of Patent: Dec. 5, 1995

[54] POLY 4-AMINOPYRROLE-2-CARBOXYAMIDE DERIVATIVES, AND PHARMACEUTICAL COMPOSITIONS WHICH CONTAIN THEM

[75] Inventors: Fabio Animati, Rome; Federico Arcamone, Nerviano; Giuseppe Giannini, Turi; Paolo Lombardi, Cesate, all of Italy

[73] Assignees: A. Menarini Industrie Farmaceutiche Riunite S.r.l., Florence; Bristol-Meyers Squibb S.p.A., Rome, both of Italy

[21] Appl. No.: 109,932

[22] Filed: Aug. 6, 1993

[30] Foreign Application Priority Data

Feb. 15, 1991 [IT] Italy ................ MI91A0404

[51] Int. Cl.$^6$ ............ A61K 31/40; C07D 207/30
[52] U.S. Cl. ............ 514/422; 514/365; 514/370; 514/374; 514/377; 514/397; 514/343; 548/194; 548/233; 548/236; 548/314.7; 548/518; 546/281
[58] Field of Search ............ 548/518, 194, 548/233, 236, 314.7; 546/281; 514/422, 365, 370, 374, 377, 397, 343

[56] References Cited

U.S. PATENT DOCUMENTS

| | | | |
|---|---|---|---|
| 3,420,845 | 1/1969 | Arcamone et al. | 548/518 |
| 4,766,142 | 8/1988 | Arcamone et al. | 514/422 |
| 4,912,199 | 3/1990 | Lown et al. | 530/331 |
| 5,049,579 | 9/1991 | Lazzari et al. | 548/518 |

FOREIGN PATENT DOCUMENTS

| | | | |
|---|---|---|---|
| 694222 | 7/1967 | Belgium | 548/518 |
| 0388948 | 9/1990 | European Pat. Off. | 548/518 |
| 1421245 | 4/1963 | France | 548/518 |
| 4019520 | 1/1991 | Germany | 548/518 |
| 1004974 | 9/1965 | United Kingdom | 548/518 |
| 2178036 | 2/1987 | United Kingdom | 548/518 |
| 9011277 | 10/1990 | WIPO | 548/537 |
| WO9214707 | 9/1992 | WIPO | 548/518 |

OTHER PUBLICATIONS

CA 67(7):32586v Amidines, Rhone–Poulenc, p. 3079, 1967.
CA 67(7):32589y 1–Alkyl-2-N-(amidinoalkyl) carbamoyl-4-acylamino-pyrroles. p. 3079, 1967.

CA 97(17):13184x Antiparasitic . . . A derivatives. Bialer et al., pp. 25–26, 1982.

J. Med. Chem. vol. 29, No. 7 (1987), pp. 1210–1214, Structure–Activity Relationship of Novel . . . Distamycin.

*Primary Examiner*—Joseph K. McKane
*Attorney, Agent, or Firm*—Hedman, Gibson & Costigan

[57] ABSTRACT

This invention relates to polyaminopyrrolecarboxyamide derivatives of general formula (I) and their pharmaceutically acceptable salts, in which A represents a chemical bond or an aromatic or heteroaromatic radical, and:
if A is a chemical bond, R is hydrogen, alkyl, dialkylaminoalkyl, alkenyl, cycloalkyl, arylalkyl, arylalkenyl, haloalkyl, or an aromatic or heteroaromatic radical;
whereas if A is an aromatic or heteroaromatic radical, R is nitro, amino or formylamino;
n is 0 or a whole number between 1 and 4;
Z is an alkylene or aromatic radical.

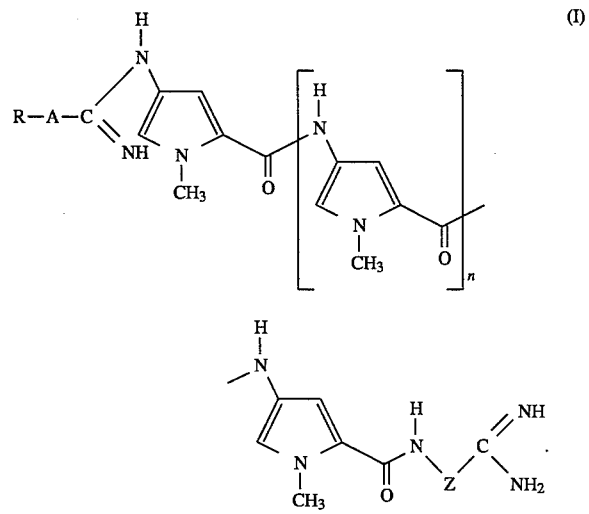

5 Claims, No Drawings

POLY

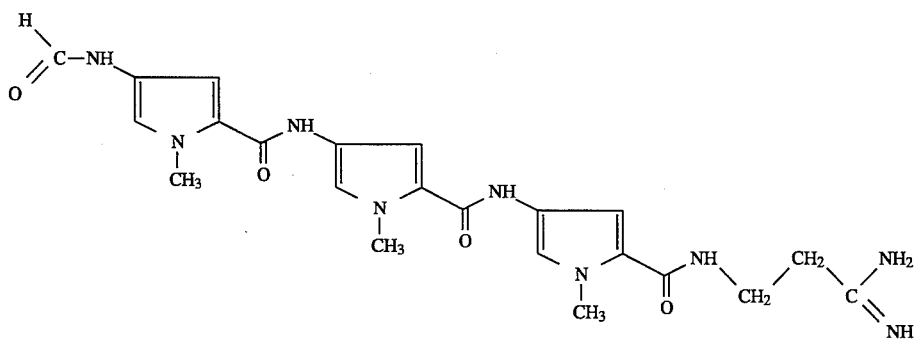

Distamycin A

4-AMINOPYRROLE-2-CARBOXYAMIDE DERIVATIVES, AND PHARMACEUTICAL COMPOSITIONS WHICH CONTAIN THEM

This application is a continuation-in-part of international PCT application No. PCT/EP92/00234 filed Feb. 4, 1992.

The applicants hereby claim the priority of PCT Application No. PCT/EP92/00234 under 35 U.S.C. 365(c) and 35 U.S.C. 120.

FIELD OF THE INVENTION

This invention relates to compounds of general formula (I)

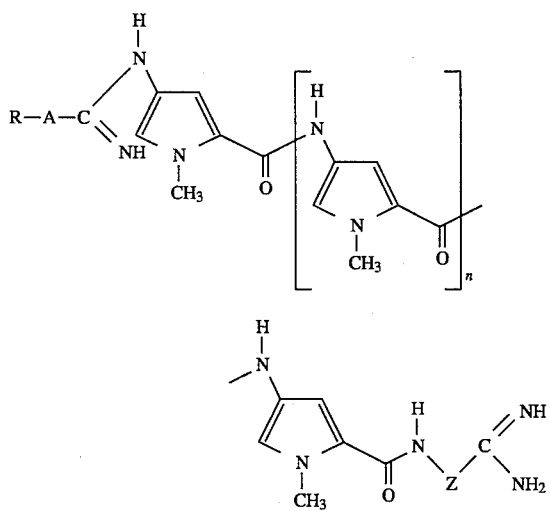

and their pharmaceutically acceptable salts, in which: A represents a chemical bond or an aromatic or heteroaromatic radical, and:

- if A is a chemical bond, R is hydrogen, alkyl, dialkylaminoalkyl, alkenyl, cycloalkyl, arylalkyl, arylalkenyl, haloalkyl, or an aromatic or heteroaromatic radical;
- whereas if A is an aromatic or heteroaromatic radical, R is nitro, amino or formylamino;
- n is 0 or a whole number between 1 and 4.;
- Z is an alkylene or aromatic radical.

STATE OF THE ART

The antiviral antibiotic distamycin A is a well known compound pertaining to the pyrrole-amidino antibiotic group and which according to the literature is able to interact reversibly and selectively with DNA-AT sequences, interfering in both the genetic message replication and transcription processes. This has been demonstrated for the corresponding synthesis analogues containing two, four, five and six pyrrolic radicals (see Arcamone, Nicoletta, Penco, Redaelli, Gazz. Chim. Ital. 99, 632, 1969) and for compounds containing a modified amidino side chain (see Arcamone, Penco, Delle Monache, Gazz. Chim. Ital. 99, 620, 1969).

However, although distamycin has interesting antiviral properties it has not found application in clinical practice as its use is limited to cutaneous infections of herpetic viruses (see F. E. Hahn in Antibiotics III, Mechanisms of Action of Antimicrobial and Antitumor Agents, by Corcoran J. W. and Hahn, F. E., Springer, New York, 1975, p.79).

In the field of products with antiviral properties the continuous provision of new drugs with a more favourable therapeutic index and a wider range of action is of particular importance, in order to adapt to the increasingly occurring infective and non-infective pathologies, and thus potentiate and widen the field of application of such drugs as much as possible.

DETAILED DESCRIPTION OF THE INVENTION

The present invention therefore provides new analogues of distamycin A in which the formyl radical is replaced by amidino radicals, which may be substituted.

The invention therefore relates to compounds of general formula (I):

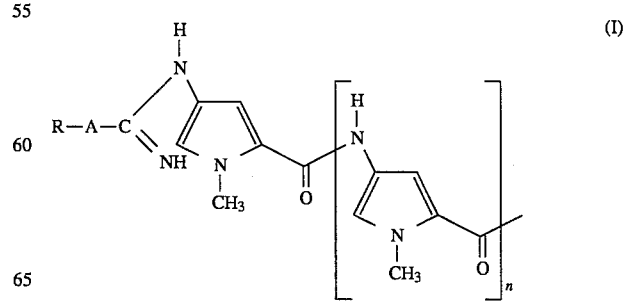

-continued

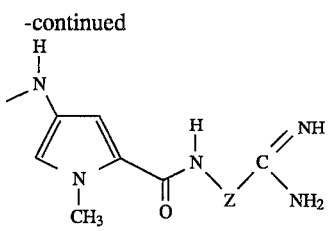

and their pharmaceutically acceptable salts, in which:
A represents a chemical bond or an aromatic or heteroaromatic radical, and:
if A is a chemical bond, R is hydrogen, alkyl, dialkylaminoalkyl, alkenyl, cycloalkyl, arylalkyl, arylalkenyl, haloalkyl, or an aromatic or heteroaromatic radical;
whereas if A is an aromatic or heteroaromatic radical, R is nitro, amino or formylamino;
n is 0 or a whole number between 1 and 4;

More specifically, the present invention relates to compounds of formula (I) in which:
n is as heretofore defined;
A is a chemical bond or an aromatic or heteroaromatic radical containing one or more nitrogen, oxygen or sulphur atoms, which can be the same or different;
R is H, $C_{1-18}$ alkyl, $C_{2-6}$ alkenyl, $C_{1-3}$ dialkylamino-$(C_{1-4})$alkyl. $C_{3-7}$ cycloalkyl, phenyl-$(C_{1-4})$alkyl, phenyl-$(C_{2-4})$alkenyl, halo-$(C_{1-18})$alkyl, phenyl, heterocyclo containing one or more nitrogen, oxygen or sulphur atoms which can be the same or different, nitro, amino or formylamino;
Z is a $C_{1-6}$ alkylene radical or an o-phenyl, m-phenyl or p-phenyl radical.

The preferred compounds of those defined by the present invention are those in which:
n is as heretofore defined;
R is H. methyl, ethyl, propyl, butyl, dodecyl, hexadecyl, octadecyl, possibly substituted by fluorine and/or chlorine, ethylene, propylene, N,N-3-dimethylaminoethyl, cyclopropyl, cyclopentyl, cyclohexyl, benzyl, styryl, phenyl, 1-methylpyrrole, nitro, amino or formylamino;
A is p-phenylene, pyrrole, 1-methylpyrrole, furan, thiophene, thiazole, pyridine, oxazole or imidazole;
Z is methylene, ethylene, propylene or p-phenylene;

By way of non-limiting example the present invention relates to the following compounds:
N-deformyl-N-formimidoyl distamycin and its salts;
N-deformyl-N-acetimidoyl distamycin and its salts;
N-deformyl-N-(chloroacetimidoyl) distamycin and its salts;
N-deformyl-N-(trichloroacetimidoyl) distamycin and its salts;
N-deformyl-N-(cyclopropanecarboxyimidoyl) distamycin and its salts;
N-deformyl-N-(acrylimidoyl) distamycin and its salts;
N-deformyl-N-cinnamidoyl distamycin and its salts;
N-deformyl-N-(3-N',N'-dimethylamino-propaneimidoyl) distamycin and its salts;
N-deformyl-N-benzimidoyl distamycin and its salts;
N-deformyl-N-(p-nitrobenzimidoyl) distamycin and its salts;
N-deformyl-N-(p-aminobenzimidoyl) distamycin and its salts;
N-deformyl-N-(p-formylaminobenzimidoyl) distamycin and its salts;
N-deformyl-N-(1-methyl-2-pyrrolecarboxyimidoyl) distamycin and its salts;
N-deformyl-N-(1-methyl-4-nitro-2-pyrrolecarboxyimidoyl) distamycin and its salts;
N-deformyl-N-(1-methyl-4-amino-2-pyrrolecarboxyimidoyl) distamycin and its salts;
N-deformyl-N-(1-methyl-4-formylamino-2-pyrrolecarboxyimidoyl) distamycin and its salts.

The present invention also relates to pharmaceutical compositions containing as active principle the products of formula (I) or the respective pharmaceutically acceptable salts formed with inorganic acids such as hydrochloric, hydrobromic, sulphuric, nitric or the like, or with organic acids such as acetic, propionic, succinic, malonic, citric, tartaric, maleic, fumaric, methanesulphonic, ethanesulphonic or p-toluenesulphonic.

The compounds of formula (I) according to the invention are prepared in accordance with one or more of the following reaction steps:

A) reacting a compound of formula (II)

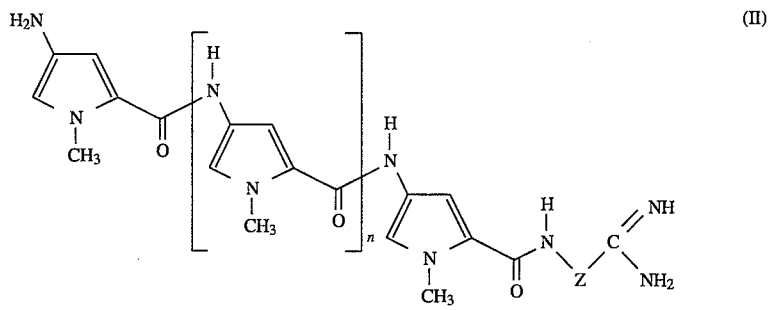

with a compound of formula (III)

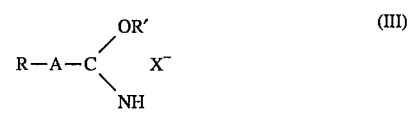

in which R, A, n and Z have the aforesaid meanings, but excluding those compounds of formula (III) in which R is amino or formylamino, R' is an alkyl radical, preferably methyl or ethyl, and $X^-$ is an anion, preferably chloride or tetrafluoroborate, to thus obtain a compound of formula (I) in which R, A, n and Z are as heretofore defined, but excluding those cases in which T is amino or formylamino;

B) reducing a compound of formula (I) in which R is nitro, A has the meaning corresponding to that value of R, and n and Z are as heretofore defined, to thus obtain a compound of formula (I) in which R is NH2 and A, n and Z are as defined;

C) formylating a compound of formula (I) in which R is $NH_2$ and A represents the values defined for R=$NH_2$, and n and Z are as heretofore defined, to thus obtain a compound of formula (I) in which R is formylamino and A, n and Z are as heretofore defined.

The compounds of formula (II) in which:

n is 0, 2, 3 or 4,

Z is methylene, propylene, p-phenylene, m-phenylene, or o-phenylene, are new and as such are covered by the present invention.

These compounds can be prepared by the general methods described for example in F. Arcamone et. al., Gazz. Chim. It., 99, 620, (1969), or F. Arcamone et. al., Gazz. Chim. It., 99, 632, (1969).

The reaction between a dihydrochloride compound of formula (II) and a compound of formula (III) (step A) is conducted preferably in the presence of a solvent and preferably using an excess of the compound of formula (III), for example between about 1.1 and about 5 moles of compound (III) per mole of compound (II). The solvent can be for example water, aliphatic alcohol (such as methanol or ethanol) or an inert organic solvent (such as tetrahydrofuran, dioxane, dimethoxyethane) in the presence of an organic base such as a tertiary amine (for example triethylamine or diisopropylamine) or an inorganic base such as sodium or potassium hydroxide, sodium or potassium carbonate, or sodium or potassium bicarbonate.

The reaction temperature is between about −10° C. and 80° C. and the reaction time can vary from about 12 hours to about 6 days.

A compound of formula (I) in which R is NO2 (obtained in accordance with step A) can be reduced (step B) for example by catalytic hydrogenation in accordance with known procedures, using for example palladium on carbon, platinum, rhodium or Raney nickel. The reduction can be effected at ambient temperature and pressure in an inert solvent such as methanol, ethanol or dimethylformamide in the presence of 10% of palladium on carbon.

A compound of formula (I) in which R is $NH_2$ (obtained in accordance with step B) can be formylated (step C) for example with the mixed anhydride of formic and acetic acid in the presence of a tertiary amine such as pyridine or triethylamine, or with N-formylimidazole obtained from carbonyldiimidazole and formic acid as described for example in J. Org. Chem. (1985), 50, 3774–3779 or with formamide and ethylformate as described in Gazz. Chim. It. 99, 632 (1972).

The compounds of formula (III) are either known compounds or can be easily prepared by known processes starting from known products. For example, compounds of formula (III) in which R' is methyl or ethyl and X- is chlorine can be prepared by the Pinner synthesis, and compounds of formula (III) in which R' is ethyl and $X^-$ is a $BF_4^-$ radical can be prepared as described in J. Org. Chem. 33, 1679 (1968).

In the particular case of compounds (III) in which R is H, A is a chemical bond and R' is alkyl, the reaction described in Ang. Chem. Int. Edit. 6, 566 (1967) is used.

EXAMPLE 1

N-deformyl-N-formimidoyl distamycin hydrochloride (I) (R= H, A= chemical bond, Z=—$CH_2$—$CH_2$, n=1)

A mixture of N-deformyldistamycin (II) (526 mg) and sodium bicarbonate (83 mg) in anhydrous ethanol (50 ml) was treated with ethyl formimidate hydrochloride (548 mg) at 0° C. The resultant solution was stirred for one hour at 0° C. and then overnight at ambient temperature.

The solvent was evaporated under vacuum and the residue taken up with isopropanol, stirred for 30 minutes and filtered. The alcoholic solution was evaporated under vacuum and the crude product was chromatographed over $SiO_2$ ($CHCl_3$ 140, MeOH 60, HCl 3% in EtOH 2). In this manner 116 mg (yield 21%) of the required product were obtained.

NMR (DMSO)-$d_6\delta$: 6:2.63 (t, 2H); 3.51 (q, 2H); 3.84 (s, 3H); 3.86 (s, 3H); 3.90 (s, 3H); 6.93–7.25 (m, 6H); 8.13 (s, 1H); 8.28 (t, 3H); 8.5–9.1 (b, 7H); 9.95 and 10.17 (2s, 2H).

EXAMPLE 2

N-deformyl-N-acetimidoyl distamycin hydrochloride (I) (R = Me, A= chemical bond, Z=—$CH_2$—$CH_2$, n=1)

A mixture of N-deformyl distamycin (160 mg), sodium bicarbonate (25 mg) and ethylacetimidate hydrochloride (56 mg) [prepared in accordance with Organic Synthesis Coll. Vol. I, p.5] in methanol (40 ml) was stirred at ambient temperature for 20 hours, the solvent was evaporated under vacuum and the residue taken up with isopropanol 9/ethanol 1, stirred for 30 minutes and filtered. The alcoholic solution was evaporated under vacuum and the crude product was chromatographed over neutral $Al_2O_3$ (EtOH 95° C.) to give 112 mg (yield 65%) of the required product.

NMR (DMSO)-$d_6\delta$: 2.30 (s, 3H); 2.63 (t, 2H); 3.5 (q, 2H); 3.80 (s, 3H); 3.83 (s, 3H); 3.90 (s, 3H); 6.94–7.28 (m, 6H); 8.24 (t, H); 8.40 and 8.62 (2bs, 2H); 8.74 and 9.05 (2bs, 4H); 9.55 (bs, 1H); 9.96 and 10.2 (2s, 2H).

EXAMPLE 3

N-deformyl-N-(1-methyl-4-nitro-2-pyrrolecarboxyimidoyl) distamycin hydrochloride (I) (R= nitro, A= N-methylpyrrole, Z=—$(CH_2)_2$—, n=1)

A mixture of N-deformyl distamycin (II) (105 mg), sodium bicarbonate (17 mg) and ethyl-1-methyl-4-nitro-2-pyrrole-carboxyimidate hydrochloride (70 mg) [prepared from 1-methyl-4-nitro-pyrrolecarbonitrile (Can. Journ. of Chem. 37, 2053 (1959) see Organic Synthesis Coil. Vol. I, p.5] in methanol (20 ml) was stirred at ambient temperature for 72 hours. To this mixture there was then added a mixture of ammonium chloride (16 mg) and sodium hydroxide (12mg) in 0.5 ml of methanol and the resultant solution was stirred for 72 hours at ambient temperature. The solvent was evaporated under vacuum and the residue chromatographed over $SiO_2$ ($CHCl_3$ 15, MeOH 5, 1N HCl 0.5) to give 57 mg (yield 42%) of the required product.

NMR (DMSO)-$d_6$ $\delta$:2.62 (t, 2H); 3.52 (q, 2H); 3.90–3.98 (m, 6H); 6.94–7.48 (m, 6H); 8.27–8.42 (m, 3H); 8.77 (bs, 2H); 9.07 (bs, 3H); 9.40 (bs 1H) 9.99 (bs, 2H); 10.29 (s, 1H).

The present invention also relates to pharmaceutical compositions containing as active principle a poly 4-aminopyrrole-2-carboxyamide derivative of formula (I) or a pharmaceutically acceptable salt thereof, and a pharmaceutically acceptable vector or diluent. A therapeutically effective quantity of a compound according to the invention is combined with an inert vector. Conventional vectors can be used and the composition can be formulated in the conventional manner. The compounds according to the invention are useful in therapeutic treatment of the human or animal body.

In particular, compositions containing the compounds of the invention are useful as antiviral and/or antitumor agents when administered to the patient in a therapeutically effective quantity of active compound.

In particular the compounds according to the invention can be employed against DNA viruses, such as herpes simplex, Sarcoma viruses, Leukemia viruses, Malonei sarcoma viruses and the like. The compounds may also be used to inhibit the growth of various tumors such as carcinomas, e.g. mammary carcinoma, lung carcinoma, bladder carcinoma, colon carcinoma, ovarian and endometrial tumors and tumors of soft tissues, bone tumors, sarcomas and leukemias. The compounds may be administered in conjunction with conventional carriers using known techniques. The compounds may be administered parenterally such as by intravenous injection or infusion or intramuscularly, subcutaneously; or orally or topically depending on the particular condition that is being treated.

A suitable dosage for administration to adult humans may range from about 0.1 to 100 mg per dose given one to four times a day. The compounds of the invention may be used and prepared for use in the same manner that the compounds of GB patent 2 178 036 A, page 5,; U.S. Pat. No. 4,766,142 and U.S. Pat. No. 4,912,199, which are incorporated by reference, are prepared and used.

We claim:

1. Compounds of general formula (I)

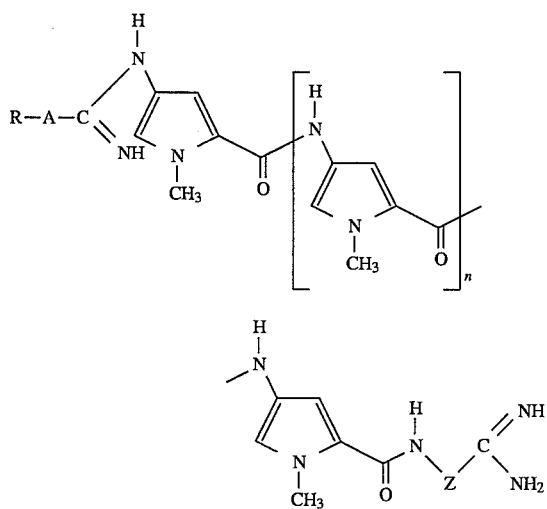

in which:

A represents a chemical bond or an aromatic or heteroaromatic radical, and:

if A is a chemical bond, R is hydrogen, alkyl, dialkylaminoalkyl, alkenyl, cycloalkyl, arylalkyl, arylalkenyl, haloalkyl, or an aromatic or heteroaromatic radical; whereas if A is an aromatic or heteroaromatic radical, R is nitro, amino or formylamino;

n is 0 or a whole number between 1 and 4;

Z is an alkylene or aromatic radical.

2. A compound as claimed in claim 1, wherein:

n is as heretofore defined;

A is a chemical bond or an aromatic or heteroaromatic radical containing one or more nitrogen, oxygen or sulphur atoms, which can be the same or different;

R is H, $C_{1-18}$ alkyl, $C_{2-6}$ alkenyl, $C_{1-3}$ dialkylamino-$(C_{1-4})$alkyl. $C_{3-7}$ cycloalkyl, phenyl-$(C_{1-4})$alkyl, phenyl-$(C_{2-4})$alkenyl, halo-$(C_{1-18})$alkyl, phenyl, heterocyclo containing one or more nitrogen, oxygen or sulphur atoms which can be the same or different, nitro, amino or formylamino;

Z is a $C_{1-6}$ alkylene radical or an o-phenyl, m-phenyl or p-phenyl radical.

3. A compound as claimed in claim 1 or 2, wherein n is as heretofore defined; R is H, methyl, ethyl, propyl, butyl, dodecyl, hexadecyl, octadecyl, which may be substituted by fluorine and/or chlorine, ethylene, propylene, N,N-3-dimethylaminoethyl, cyclopropyl, cyclopentyl, cyclohexyl, benzyl, styryl, phenyl, 1-methylpyrrole, nitro, amino or formylamino; A is p-phenylene, pyrrole, 1-methylpyrrole, furan, thiophene, thiazole, pyridine, oxazole or imidazole; Z is methylene, ethylene, propylene or p-phenylene.

4. A compound as claimed in claim 1, consisting of:

N-deformyl-N-formimidoyl distamycin and its salts;

N-deformyl-N-acetimidoyl distamycin and its salts;

N-deformyl-N-(chloroacetimidoyl) distamycin and its salts;

N-deformyl-N-(trichloroacetimidoyl) distamycin and its salts;

N-deformyl-N-(cyclopropanecarbioxyimidoyl) distamycin and its salts;

N-deformyl-N-(acrylimidoyl) distamycin and its salts;

N-deformyl-N-cinnamidoyl distamycin and its salts;

N-deformyl-N-(3-N',N'-dimethylamino-propaneimidoyl) distamycin and its salts;

N-deformyl-N-benzimidoyl distamycin and its salts;

N-deformyl-N-(p-nitrobenzimidoyl) distamycin and its salts;

N-deformyl-N-(p-aminobenzimidoyl) distamycin and its salts;

N-deformyl-N-(p-formylaminobenzimidoyl) distamycin and its salts;

N-deformyl-N-(1-methyl-2-pyrrolecarboxyimidoyl) distamycin and its salts;

N-deformyl-N-(1-methyl-4-nitro-2-pyrrolecarboxyimidoyl) distamycin and its salts;

N-deformyl-N-(1-methyl-4-amino-2-pyrrolecarboxyimidoyl) distamycin and its salts;and N-deformyl-N-(1-methyl-4-formylamino-2-pyrrolecarboxyimidoyl distamycin and its salts.

5. Pharmaceutical compositions containing as active principle a compound of formula (I) claimed in claim 1 or a pharmaceutically acceptable salt thereof, and a diluent.

* * * * *